(12) United States Patent
Noda et al.

(10) Patent No.: US 9,877,808 B2
(45) Date of Patent: Jan. 30, 2018

(54) MEMBRANE FOR INDUCING REGENERATION OF BONE/TISSUE, AND METHOD FOR PRODUCING SAME

(71) Applicant: HITACHI CHEMICAL COMPANY, LTD., Tokyo (JP)

(72) Inventors: Hiroko Noda, Tsukuba (JP); Tetsushi Maruyama, Tsukuba (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 245 days.

(21) Appl. No.: 14/362,425

(22) PCT Filed: Nov. 30, 2012

(86) PCT No.: PCT/JP2012/081081
§ 371 (c)(1),
(2) Date: Jun. 3, 2014

(87) PCT Pub. No.: WO2013/084817
PCT Pub. Date: Jun. 13, 2013

(65) Prior Publication Data
US 2014/0315149 A1    Oct. 23, 2014

(30) Foreign Application Priority Data

Dec. 5, 2011   (JP) ................. 2011-265633

(51) Int. Cl.
*A61C 8/00*    (2006.01)
*A61C 8/02*    (2006.01)
(Continued)

(52) U.S. Cl.
CPC ........ *A61C 8/0013* (2013.01); *A61C 8/0006* (2013.01); *A61L 31/06* (2013.01);
(Continued)

(58) Field of Classification Search
CPC ........ A61F 2/4644; A61F 2/28; A61F 2/2846; A61F 2/4601; A61C 8/0013
See application file for complete search history.

(56) References Cited

U.S. PATENT DOCUMENTS 5,899,939 A * 5/1999 Boyce .................. A61F 2/28
                                                                                523/113
6,863,694 B1 * 3/2005 Boyce .................. A61B 17/80
                                                                                623/23.61
(Continued)

FOREIGN PATENT DOCUMENTS

CN     101947334 A    1/2011
CN     102145194 A    8/2011
(Continued)

OTHER PUBLICATIONS

Database WPI Week 200414 Thomson Scientific, Aug. 27, 2003, XP002741034.
(Continued)

*Primary Examiner* — Yogesh Patel
(74) *Attorney, Agent, or Firm* — Fitch, Even, Tabin & Flannery LLP

(57) ABSTRACT

The present invention provides a membrane for guided regeneration of bone and tissue comprising an organic base material and a new bone formation guide layer on one or both sides of the organic base material, the new bone formation guide layer containing a hydrophilic polymer and calcium phosphate.

16 Claims, 2 Drawing Sheets

(51) Int. Cl.
  *A61L 31/06* (2006.01)
  *A61L 31/08* (2006.01)
  *A61L 31/10* (2006.01)
(52) U.S. Cl.
  CPC ............ *A61L 31/086* (2013.01); *A61L 31/10* (2013.01); *A61L 2430/02* (2013.01)

(56) References Cited

U.S. PATENT DOCUMENTS

| | | | | |
|---|---|---|---|---|
| 8,524,265 | B2* | 9/2013 | McKay | A61B 17/58 424/423 |
| 2003/0147935 | A1* | 8/2003 | Binette | A61F 2/0063 424/423 |
| 2008/0147197 | A1 | 6/2008 | McKay | |
| 2009/0060978 | A1* | 3/2009 | Bluecher | A61L 31/041 424/426 |
| 2010/0119564 | A1* | 5/2010 | Kasuga | A61L 31/06 424/402 |

FOREIGN PATENT DOCUMENTS

| | | |
|---|---|---|
| DE | 19654884 A1 | 9/1997 |
| EP | 1757315 A1 | 2/2007 |
| JP | 02-241460 | 9/1990 |
| JP | 06-304240 | 11/1994 |
| JP | 07-236688 | 9/1995 |
| JP | 2001514565 | 9/2001 |
| JP | 2003-190271 A | 7/2003 |
| JP | 2007-098117 A | 4/2007 |
| JP | 2007-160011 | 6/2007 |
| JP | 2007159935 A | 6/2007 |
| JP | 2010-273847 | 12/2010 |
| KR | 2012-0010506 A | 2/2012 |
| WO | 2009/054609 A | 4/2009 |
| WO | WO 2011/155243 | 12/2011 |

OTHER PUBLICATIONS

Extended Search Report issued by the European Patent Office dated Jul. 1, 2015, in regards European Application No. 12856247.7.
Office Action dated Oct. 8, 2015, by the State Intellectual Property Office of the People's Republic of China in regards Chinese Application No. 201280056938.4.
Korean Intellectual Property Office, Office Action dated Jan. 21, 2016, from corresponding Korean Patent Application 10-2014-7011564, 4 pages.
Japanese Office Action for Japanese Patent Application No. 2013-548210 dated Mar. 24, 2015.
International Preliminary Report on Patentability dated Jun. 19, 2014, corresponding to International Application No. PCT/JP2012/081081.
T. Noriko, et al., "Preparation and Application of PET/collagen/hydroxyapatite membrane to guided bone regeneration", Abstracts from the Journal of the Ceramic Society of Japan, p. 288.
T. Furusawa, et al., "Kayosei Rinsan Calcium (SCP) Coat hikyushusei Membrane no GBR Koka, vol. 33$^{rd}$, enter text", The Annual Meeting of the Japanese Society for Biomaterials Yokoshu, Nov. 2011, p. 291.
Notice of Allowance issued by the Korean Intellectual Property Office dated Oct. 3, 2016, in regards to Korean Patent Application No. 10-2014-7011564.

* cited by examiner

MEMBRANE FOR INDUCING REGENERATION OF BONE/TISSUE, AND METHOD FOR PRODUCING SAME

TECHNICAL FIELD

The present invention relates to a membrane for guided regeneration of bone and tissue (membrane for guided bone/tissue regeneration) that separates granulation tissue from the site where bone is to be regenerated at a site of bone loss, prevents infiltration of granulation tissue into the site where bone is to be regenerated, and generates components of the same material as bone at the site of bone loss.

BACKGROUND ART

When a portion of bone is lost due to injury or a bone-eroding condition, the person experiencing bone loss is forced to adopt a different lifestyle than before the bone loss. High benefit is provided by technologies allowing persons that have experienced bone loss to carry on activities similar to before bone loss. In the case of teeth, which are at high risk of being lost by aging or disease, partial dentures or implant are used as substitutes for lost teeth. However, problems arise in that hard foods cannot be eaten with partial dentures, while effort is also necessary for the unavoidable daily removal and cleaning. With implant, on the other hand, new teeth are established and therefore almost no change is necessary to dietary habits, compared to partial dentures and the like.

Implant is a method in which a screw-shaped object known as a fixture is implanted in the hole opened in alveolar bone following tooth extraction, in place of a tooth, and after being fused, a prosthesis is mounted over the fused fixture. When fusing the fixture, it is desirable for the gap between the fixture and the alveolar bone to be firmly filled with regenerated bone. Methods have been established for regenerating bone-equivalent components in the gap between fixtures and alveolar bone, such methods being known as Guided Bone Regeneration (GBR).

In GBR, a fixture must be fused to alveolar bone. If the fixture does not become fused to the alveolar bone, then even if the prosthesis is mounted on the fixture, the fixture may become loose resulting in poor dental meshing and difficulty in eating food. Consequently, fusing the fixture to alveolar bone is the most important step in implant operations. In this step, a hole is opened in the alveolar bone and then a membrane must be used to produce regenerated bone in the alveolar bone. The period of regenerated bone production is the period in which the implant has not been completed and the patient feels a burden on routine dietary habits, and it is therefore desirable to produce regenerated bone more rapidly. Normally, 3 to 9 months is required for production of regenerated bone.

Membranes used in GBR methods include absorbable membranes and non-absorbable membranes. In regard to non-absorbable membranes, Non-Patent Literature 1 discloses a PET/collagen/hydroxyapatite membrane. Absorbable membranes, on the other hand, include membranes made of collagen, and membranes made of human skin.

CITATION LIST

Non-Patent Literature

[Non-Patent Literature 1] Abstracts from the Journal of The Ceramic Society of Japan, p288

SUMMARY OF INVENTION

Problems to be Solved by the Invention

The non-absorbable membrane disclosed in Non-Patent Literature 1 is fabricated by forming amide bonds (peptide bonds) from collagen onto the surface of PET using water-soluble carbodiimide (WSC), and then immobilizing urease on the surface, and depositing hydroxyapatite from urea, a calcium source and a phosphorus source. The fabrication method for the membrane of Non-Patent Literature 1 is extremely complex. In addition, it is difficult for membranes fabricated by the method to be formed into thick films, and when formed thick, the membranes have had the drawback of peeling from the PET.

Absorbable membranes, on the other hand, cannot completely separate regenerated bone forming sites from granulation tissue, and therefore granulation tissue infiltrates into the regenerated bone forming sites and interferes with production of regenerated bone. Furthermore, with an absorbable membrane, the bone and membrane and granulation tissue produce accretion, making it difficult to embed the fixture. In addition, with an absorbable membrane it is difficult to confirm formation of regenerated bone from outside the oral cavity during clinical examination. Also, absorbable membranes are very expensive, costing 2000 yen/cm$^2$ at the low end and more than 15,000 yen/cm$^2$ at the high end, and therefore the patient must also bear a financial burden.

Such membranes are problematic because they require time for fabrication and are difficult to manage during operations, while time is also required for production of regenerated bone. In particular, the time required for production of regenerated bone allows proliferation of bacteria at the regenerated bone production site, sometimes making it impossible to accomplish bone regeneration and also producing halitosis, and this often necessitates a second operation for the patient. This results in creation of the burden of even more time and cost for the patient.

The present invention has been accomplished in light of these problems associated with the prior art, and its object is to provide a membrane for guided regeneration of bone and tissue that is easily manageable and can shorten the time necessary for regenerated bone production, as well as a method for producing the membrane.

Means for Solving the Problems

The present invention provides a membrane for guided regeneration of bone and tissue comprising an organic base material and a new bone formation guide layer on one or both sides of the organic base material, the new bone formation guide layer containing a hydrophilic polymer and calcium phosphate.

The membrane for guided regeneration of bone and tissue according to the present invention has excellent manageability due to this construction. Furthermore, it exhibits excellent performance in guiding regeneration of bone tissue, and can significantly shorten the time required for regenerated bone production. The term "regenerated bone" as used herein refers to bone regenerated at sites that have experienced bone loss, but it is also interchangeable with the term "new bone formation" in the sense that bone can be newly formed at sites where no bone is present.

The thickness of the new bone formation guide layer in the membrane for guided regeneration of bone and tissue is preferably 10 to 200 μm. If the thickness of the new bone formation guide layer is within this range, it will be possible to further shorten the time required for regenerated bone production, and to more effectively inhibit detachment of the new bone formation guide layer from the organic base material when the membrane is set in a site where bone tissue is to be regenerated (the site of interest), to obtain a more manageable membrane.

In the membrane for guided regeneration of bone and tissue, the proportion of the contents of the hydrophilic polymer and the calcium phosphate in the new bone formation guide layer is preferably 40:60 to 10:90 as the mass ratio. If the content ratio is within this range, the regenerated bone guide layer will have more excellent adhesiveness on the organic base material and even greater manageability, and it will be possible to yet further shorten the time required for regenerated bone production.

The membrane for guided regeneration of bone and tissue can be suitably used for dental treatment including implants.

The present invention also provides a method for producing a membrane for guided regeneration of bone and tissue comprising a step of coating an organic base material with a mixture comprising a hydrophilic polymer and calcium phosphate. The membrane for guided regeneration of bone and tissue described above can be produced by the production method of the present invention. Furthermore, production of a membrane for guided regeneration of bone and tissue is possible by a simple procedure, and production cost can be reduced.

The production method may further comprise a step of roughening treatment of the surface of the organic base material. This will result in more firm bonding between the organic base material and the new bone formation guide layer.

Effects of the Invention

Because the membrane for guided regeneration of bone and tissue of the present invention is highly manageable and allows regenerated bone production to be achieved more easily in a shorter period, it can shorten the time for establishing implants. Also, according to the production method of the present invention it is possible to produce the membrane for guided regeneration of bone and tissue described above. The production method of the present invention employs coating a hydrophilic polymer and calcium phosphate on the surface of an organic base material, and it is therefore easy and cost-reducing.

EMBODIMENTS FOR CARRYING OUT THE INVENTION

The membrane of this embodiment comprises an organic base material and a new bone formation guide layer on one or both sides of the organic base material. The new bone formation guide layer comprises a hydrophilic polymer and calcium phosphate. The membrane of this embodiment can be used for bone regeneration in a GBR method for implant treatment, for example.

Figure 1:
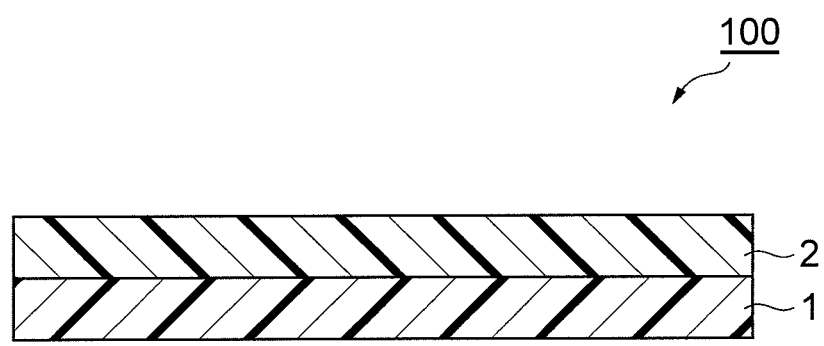
FIG. 1 is a schematic cross-sectional view of a membrane for guided regeneration of bone and tissue according to an embodiment of the present invention.

FIG. 1 is a schematic cross-sectional view of a membrane for guided regeneration of bone and tissue according to an embodiment of the invention. The membrane for guided regeneration of bone and tissue 100 shown in FIG. 1 comprises an organic base material 1 and a new bone formation guide layer 2 on one side of the organic base material 1.

Figure 2:
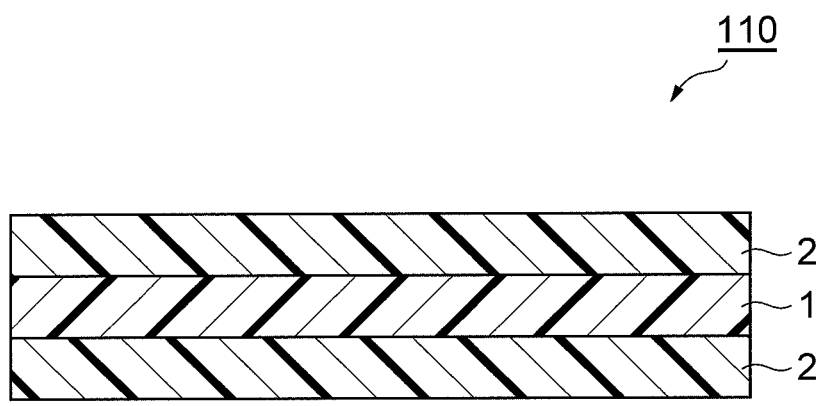
FIG. 2 is a schematic cross-sectional view of a membrane for guided regeneration of bone and tissue according to an embodiment of the present invention.

FIG. 2 is a schematic cross-sectional view of a membrane for guided regeneration of bone and tissue according to another embodiment. The membrane for guided regeneration of bone and tissue 110 shown in FIG. 2 comprises an organic base material 1 and two new bone formation guide layers 2 on both sides of the organic base material 1.

[Organic Base Material]

The organic base material for this embodiment is not particularly restricted so long as it is a base material that is non-bioabsorbable and is composed of an organic substance. That is, the membrane of this embodiment is a non-absorbable membrane. There are no particular restrictions on the shape of the base material, but from the viewpoint of handleability as a membrane, it is preferably in the form of a sheet or film.

The organic base material is preferably polyethylene (PE), polystyrene (PS) or polyethylene terephthalate (PET), and more preferably PET. PE, PS and PET are optimal substances because they undergo minimal discoloration and deterioration when sterilized by γ-ray irradiation at 25 kGy to 50 kGy, and are stable substances. Polyvinyl chloride (PVC), polycarbonate (PC), polyamide (nylon/PA), polymethyl methacrylate (PMMA), epoxy resins and urethane resins may also be used instead of PE, PS or PET, because they undergo minimal deterioration under γ-ray irradiation. Most suitable among these are organic base materials that do not cause major problems when situated in the body as GBR membranes, for example. Also preferred among these are materials that are inexpensive and easily obtainable, to alleviate treatment cost. PET is advantageous as it is relatively available, is biologically inactive and has low accretion with surrounding tissue, and since it is not a porous material it is resistant to infiltration of bacteria and immobilization of bacteria. Therefore, among PE, PS and PET it is more preferred to use PET. These organic base materials may be used alone. Alternatively, a base material comprising these organic base materials in double or triple layers may be used.

[Hydrophilic Polymer]

The hydrophilic polymer for this embodiment may be a commonly marketed hydrophilic polymer. Specifically, examples of hydrophilic polymers include polysaccharides, proteins such as collagen, denatured proteins such as gelatin, peptides such as collagen peptide, and nucleic acids. Of these, gelatin, collagen and collagen peptides are preferred. Those with low endotoxicity are preferred and low-endotoxin gelatin is even more preferred. The hydrophilic polymer used may be of a single type, or it may be a combination of two or more types.

Collagen is an organic component of bone and is highly biocompatible. While, gelatin is less expensive and more easily obtainable than collagen. In addition, gelatin has a satisfactory performance record, being used for medicine capsules in pharmaceuticals.

Gelatin is a denatured form of collagen, an organic material component of bone. Specifically, gelatin is a randomly coiled protein resulting from destruction of the triple helix structure of collagen by heat or by using an acid or alkali. Gelatin has the same primary structure as collagen. Thus, when gelatin is applied in the body as a medical material, it exhibits the same high affinity for tissue and high biodegradability as collagen. Gelatin generally contains a substantial amount of endotoxin introduced from the starting material and by contamination during production. Endotoxin is a constituent component of the outer membranes of gram-negative bacteria, and while posing no problem when ingested orally, it exhibits various physiological activity when it enters the bloodstream. In particular, macrophages are strongly stimulated by endotoxin to produce inflammatory cytokines and nitrogen monoxide, leading to fever and related symptoms. It is therefore preferred to use low-endotoxin gelatin. Any generally marketed low-endotoxin gelatin may be used, but it preferably has a minimum heat value of no greater than 5 EU.

The hydrophilic polymer may be a polymer containing phosphate residues.

[Calcium Phosphate]

Calcium phosphate in a variety of different forms may be used as the calcium phosphate. Examples of calcium phosphate include simple calcium phosphate ($Ca_3(PO_4)_2$; TCP), as well as monocalcium phosphate ($CaHPO_4$), calcium dihydrogenphosphate ($Ca(H_2PO_4)_2$), amorphous calcium phosphate $Ca_3(PO_4)_2 \cdot nH_2O$; ACP) and octacalcium phosphate ($Ca_8H_2(PO_4)_6 \cdot 5H_2O$ OCP). They may also be compounds containing calcium element and phosphate groups.

Calcium phosphate is gradually transformed in the presence of water, eventually being converted to crystals with an apatite structure. The apatite is preferably apatite represented by formula (1), since this has properties similar to those of teeth.

$$Ca_{(10-m)}M_m(PO_4)_6X_2 \quad (1)$$

[In formula (1), M represents one or more divalent cations, m represents an integer of 0 to 5 and X represents a monovalent anion.]

The apatite is more preferably hydroxyapatite of formula (1) wherein m=0 and X=OH ($Ca_{10}(PO_4)_6(OH)_2$; HAP).

In formula (1), M may be strontium ion, barium ion, magnesium ion or the like, or it may be two hydrogen atoms (2H). The calcium phosphate may be a material that transforms to a mixture of hydroxyapatite and apatite with the structure of formula (1) where X is a fluorine ion or apatite with a structure where M is a magnesium ion. A structure where X is a fluorine ion and M is a magnesium ion in formula (1) can approximate the actual structure of teeth.

Also, the calcium phosphate need only be a material having properties equivalent to those of bone, and in addition to artificial inorganic compounds, there may be used demineralized freeze-dried bone allografts.

The calcium phosphate used may be of a single type alone, or a mixture of calcium phosphates with different compositions may be used.

The mean particle diameter of the calcium phosphate for this embodiment is preferably 50 to 200 nm. The mean particle diameter is more preferably 80 to 150 nm and even more preferably 100 to 130 nm. If the mean particle diameter of the calcium phosphate is 50 to 200 nm, the dispersibility between the calcium phosphate and hydrophilic polymer will be satisfactory and coating will be facilitated. The mean particle diameter is the particle diameter with an integrated value of 50% in the particle size distribution as determined by laser diffraction/scattering (median diameter: D50).

[Membrane]

For the membrane of this embodiment, the thickness of the new bone formation guide layer comprising the hydrophilic polymer and calcium phosphate is preferably 10 to 200 µm. If the thickness of the new bone formation guide layer is 10 to 200 µm, regenerated bone production will take place more rapidly. If the thickness is less than 10 µm, the time required for regenerated bone production will tend to be longer, and if the thickness is greater than 100 µm, the hydrophilic polymer and calcium phosphate will separate off when the membrane is set in the oral cavity and will dissipate throughout the oral cavity, and management will tend to become more difficult. The thickness of the new bone formation guide layer is more preferably 20 to 80 µm and even more preferably 30 to 60 µm. A thickness of 20 to 80 µm is more effective for regenerated bone production. With a thickness of 30 to 60 µm, there will be virtually no detachment during handling and the period for regenerated bone production will also be shortened.

The proportion of the hydrophilic polymer and calcium phosphate contents in the new bone formation guide layer of the membrane of this embodiment is preferably 40:60 to 10:90 as the mass ratio. It is more preferably 30:70 to 15:85 and even more preferably 20:80. Adhesiveness of the new bone formation guide layer onto the organic base material will tend to vary depending on the hydrophilic polymer and calcium phosphate content ratio. Better adhesiveness means a more manageable membrane. If the hydrophilic polymer and calcium phosphate content ratio is 20:80 as the mass ratio, the adhesiveness will be satisfactory and a membrane with a shorter regenerated bone production time will be obtained.

The membrane of this embodiment can be suitably used for guided bone/tissue regeneration. It is most preferably used for dental treatment purposes, and for example, it may be suitably used for bone regeneration in GBR during implant operations. It may also be used for bone regeneration treatment, in general surgical treatment. Furthermore, the biocompatibility of the membrane of this embodiment may be utilized for use as a bandage for repair of local microfractures. It may also be attached to the surface of a titanium alloy used in an artificial bone, for use as a member providing biocompatibility.

[Method for Producing Membrane]

The method for producing a membrane for guided regeneration of bone and tissue according to this embodiment comprises at least a step of coating an organic base material with a mixture comprising a hydrophilic polymer and calcium phosphate. The hydrophilic polymer, calcium phosphate and organic base material used may be those described above.

The method for producing a membrane for guided regeneration of bone and tissue according to this embodiment may further comprise a step of mixing the hydrophilic polymer and calcium phosphate to obtain a mixture comprising the hydrophilic polymer and the calcium phosphate. There are no particular restrictions on the mixing method, and for example, it may be accomplished by weighing out the hydrophilic polymer and calcium phosphate so that their content ratio is at the prescribed ratio, and then adding purified water or ion-exchanged water and carrying out mixing with a mortar, stirring rod, mechanical stirrer, magnetic stirrer or homogenizer. When components other than the hydrophilic polymer and calcium phosphate are to be used, the components may be weighed out before adding the purified water.

The organic base material described above may be directly coated over the top with the mixture of the calcium phosphate (for example, calcium phosphate containing apatite) and the hydrophilic polymer (for example, gelatin), but preferably the surface is subjected to roughening treatment by pretreating the coating surface of the organic base material (for example, the organic base material film) by sand blast treatment or corona treatment, or by coating with a porous organic base material. In other words, the method for producing a membrane for guided regeneration of bone and tissue according to this embodiment may further comprise a step of roughening treatment on the coating surface of the organic base material.

The method of roughening treatment may be a method of treating the coating surface of the organic base material with a strong alkali solution, as well as sand blast treatment or corona treatment. Moreover, the coating surface of the organic base material may be treated with a strong alkali solution after sand blast treatment or corona treatment. Also, in order to improve adhesiveness between the organic base material and the coating material, it is effective to apply a biocompatible substance onto the organic base material (for example, the organic base material film), as roughening treatment. In such cases, sodium hyaluronate or the like may be applied onto the organic base material. The organic base material used is preferably one that has been subjected to roughening treatment only on one side of the organic base material, but it is also possible to attach two organic base materials together, processing both sides by roughening treatment and then separating the two materials to obtain organic base materials that have been subjected to roughening treatment on only one side.

Also, when the organic base material is to be coated with a mixture of a hydrophilic polymer and calcium phosphate, a single-side coater may be used for application, but alternatively two organic base materials may be attached together with their non-roughened sides facing each other, and application performed using a die coater. When layering in a double fashion, thermocompression bonding may be employed with the organic base material formed into a pouch, so that the hydrophilic polymer and calcium phosphate do not infiltrate between the two non-roughened sides.

EXAMPLES

Preferred examples of this embodiment will now be described. However, the invention is not limited to the examples described below.

Example 1

(Roughening Treatment of Organic Base Material)
A PET film (E5100 by Toyobo, Ltd., 100 μm) was cut to a size of 10 cm×10 cm and dipped in a 3 mol/L sodium hydroxide aqueous solution at a temperature of 70° C. for 3 hours. After dipping, the film was removed out of the sodium hydroxide aqueous solution and rinsed with purified water to obtain a roughened PET film.

(Preparation of Calcium Phosphate and Hydrophilic Polymer Mixture)
Using hydroxyapatite (Wako Pure Chemical Industries, Ltd.) as calcium phosphate and collagen peptide (Wako Pure Chemical Industries, Ltd.) as a hydrophilic polymer, these were mixed to a calcium phosphate:hydrophilic polymer ratio of 60:40, as mass ratio, purified water was added to a solid content of 72%, and the components were mixed with a mortar to obtain a mixture of calcium phosphate and a hydrophilic polymer.

(Application of Calcium Phosphate and Hydrophilic Polymer Mixture to PET)
A mixture of calcium phosphate and a hydrophilic polymer was applied onto one side of a roughened PET film using an applicator at a gap of 100 μm (coated film thickness: 60 μm). After coating, it was dried at 60° C. for 1 hour to obtain a membrane.

(Adhesiveness Evaluation)
The fabricated membrane was subjected to an adhesiveness test, and the adhesiveness between the PET film and coated material was evaluated. The adhesiveness test was conducted in the following manner. The coated surface of the membrane was placed facing upward and 11 grid lines at 1 mm spacings were formed with a cutter. Cellophane tape with a length of 6 cm (BK-18, product of Sumitomo 3M) was attached with the edges at the sections where the grid notches had been formed. After thoroughly rubbing the top of the cellophane tape with an eraser, it was peeled off after 1 minute and the presence of any detachment of the coated material and the PET film was judged for evaluation. The evaluation criteria for adhesiveness was as follows: A: No detachment, B: slight detachment, C: Major detachment.

(Guided New Bone Formation Test)
Immediately after tooth extraction from the oral cavity of a pig, a fabricated membrane was placed over it covering the alveolar bone, and the subsequent progress was observed. Observation was made after 2 months, after 2.5 months, after 3 months, after 4 months and after 6 months, and the new bone formation period was determined.

Example 2

A membrane was fabricated in the same manner as Example 1, except that the proportion of collagen peptide was 30 mass % and the proportion of hydroxyapatite was 70 mass %, with respect to the total mixture, and an adhesiveness test and guided new bone formation test were also conducted.

Example 3

A membrane was fabricated in the same manner as Example 1, except that the proportion of collagen peptide was 20 mass % and the proportion of hydroxyapatite was 80 mass %, with respect to the total mixture, and an adhesiveness test and guided new bone formation test were also conducted.

Example 4

A membrane was fabricated in the same manner as Example 1, except that the proportion of collagen peptide was 15 mass % and the proportion of hydroxyapatite was 85 mass %, with respect to the total mixture, and an adhesiveness test and guided new bone formation test were also conducted.

Example 5

A membrane was fabricated in the same manner as Example 1, except that the proportion of collagen peptide was 10 mass % and the proportion of hydroxyapatite was 90 mass %, with respect to the total mixture, and an adhesiveness test and guided new bone formation test were also conducted.

Example 6

A membrane was fabricated in the same manner as Example 1, except that gelatin was used instead of collagen peptide, and the proportion of gelatin was 40 mass % and the proportion of hydroxyapatite was 60 mass %, with respect to the total mixture, and an adhesiveness test and guided new bone formation test were also conducted.

Example 7

A membrane was fabricated in the same manner as Example 6, except that the proportion of gelatin was 30 mass % and the proportion of hydroxyapatite was 70 mass %, with respect to the total mixture, and an adhesiveness test and guided new bone formation test were also conducted.

Example 8

A membrane was fabricated in the same manner as Example 6, except that the proportion of gelatin was 20 mass % and the proportion of hydroxyapatite was 80 mass %, with respect to the total mixture, and an adhesiveness test and guided new bone formation test were also conducted.

Example 9

A membrane was fabricated in the same manner as Example 6, except that the proportion of gelatin was 15 mass % and the proportion of hydroxyapatite was 85 mass %, with respect to the total mixture, and an adhesiveness test and guided new bone formation test were also conducted.

Example 10

A membrane was fabricated in the same manner as Example 6, except that the proportion of gelatin was 10 mass % and the proportion of hydroxyapatite was 90 mass %, with respect to the total mixture, and the post-coating film thickness was 80 μm, and an adhesiveness test and guided new bone formation test were also conducted.

Example 11

A membrane was fabricated in the same manner as Example 6, except that the proportion of gelatin was 20 mass % and the proportion of hydroxyapatite was 80 mass %, with respect to the total mixture, and the post-coating film thickness was 120 μm, and an adhesiveness test and guided new bone formation test were also conducted.

Example 12

A membrane was fabricated in the same manner as Example 6, except that the proportion of gelatin was 20 mass % and the proportion of hydroxyapatite was 80 mass %, with respect to the total mixture, while the post-coating film thickness was 10 and an adhesiveness test and guided new bone formation test were also conducted.

Example 13

A membrane was fabricated in the same manner as Example 6, except that the proportion of gelatin was 20 mass % and the proportion of hydroxyapatite was 80 mass %, with respect to the total mixture, while the post-coating film thickness was 6 μm, and an adhesiveness test and guided new bone formation test were also conducted.

The test results are summarized in Table 1. The membrane of the present invention can significantly shorten the period of new bone formation. It was also shown that membranes with collagen peptide or gelatin and hydroxyapatite mixed in a mass ratio of 20:80 and applied as mixtures (as in Example 3 and Example 8, for example) were effective as membranes with satisfactory adhesiveness and a short new bone formation period.

TABLE 1

| | Mixture composition | | | | | |
| | Hydrophilic polymer | | Calcium phosphate | | | |
| | Collagen peptide (mass %) | Gelatin (mass %) | Hydroxy-apatite (mass %) | Film thick-ness (μm) | Adhe-sive-ness | New bone formation period (months) |
|---|---|---|---|---|---|---|
| Example 1 | 40 | — | 60 | 60 | A | 4 |
| Example 2 | 30 | — | 70 | 60 | A | 3.5 |
| Example 3 | 20 | — | 80 | 60 | A | 2.5 |
| Example 4 | 15 | — | 85 | 60 | A | 2.5 |
| Example 5 | 10 | — | 90 | 60 | B | 2.5 |
| Example 6 | — | 40 | 60 | 60 | A | 3.5 |
| Example 7 | — | 30 | 70 | 60 | A | 3 |
| Example 8 | — | 20 | 80 | 60 | A | 2 |
| Example 9 | — | 15 | 85 | 60 | A | 2.5 |
| Example 10 | — | 10 | 90 | 80 | B | 2.5 |
| Example 11 | — | 20 | 80 | 120 | B | 2 |
| Example 12 | — | 20 | 80 | 10 | B | 2 |
| Example 13 | — | 20 | 80 | 6 | C | 4 |

EXPLANATION OF SYMBOLS

1: Organic base material, 2: new bone formation guide layer, 100, 110: membrane for guided regeneration of bone and tissue.

The invention claimed is:

1. A membrane for guided regeneration of bone and tissue comprising a non-bioabsorbable organic base material and a new bone formation guide layer on one or both sides of the non-bioabsorbable organic base material, the new bone formation guide layer containing a hydrophilic polymer and calcium phosphate, and having a thickness of 10 to 200 μm,
wherein the non-bioabsorbable organic base material comprises at least one of polyethylene terephthalate, polyethylene, polystyrene, polyvinyl chloride, polycarbonate, polyamide, polymethyl methacrylate, epoxy resin or urethane resin, wherein the proportion of the contents of the hydrophilic polymer and the calcium phosphate in the new bone formation guide layer is 40:60 to 10:90 as the mass ratio.

2. The membrane for guided regeneration of bone and tissue according to claim 1, which is for dental treatment.

3. The membrane for guided regeneration of bone and tissue according to claim 1, produced by coating an organic base material with a mixture comprising a hydrophilic polymer and calcium phosphate.

4. The membrane for guided regeneration of bone and tissue according to claim 1, which is for dental treatment.

5. The membrane for guided regeneration of bone and tissue according to claim 1, wherein the new bone formation guide layer has a thickness of 20 to 80 μm.

6. The membrane for guided regeneration of bone and tissue according to claim 1, wherein the new bone formation guide layer has a thickness of 30 to 60 μm.

7. The membrane for guided regeneration of bone and tissue according to claim 1, wherein the proportion of the contents of the hydrophilic polymer and the calcium phosphate in the new bone formation guide layer is 30:70 to 15:85 as the mass ratio.

8. The membrane for guided regeneration of bone and tissue according to claim 1, wherein the membrane consists of the non-bioabsorbable organic base material and the new bone formation guide layer on one side of the non-bioabsorbable organic base material.

9. The membrane for guided regeneration of bone and tissue according to claim 1, wherein the membrane consists of the non-bioabsorbable organic base material and the new bone formation guide layer on both sides of the non-bioabsorbable organic base material.

10. A method for producing a membrane for guided regeneration of bone and tissue comprising a step of coating a non-bioabsorbable organic base material with a mixture comprising a hydrophilic polymer and calcium phosphate and having a thickness of 10 to 200 μm
wherein the non-bioabsorbable organic base material comprises at least one of polyethylene terephthalate, polyethylene, polystyrene, polyvinyl chloride, polycarbonate, polyamide, polymethyl methacrylate, epoxy resin or urethane resin, wherein the proportion of the contents of the hydrophilic polymer and the calcium phosphate in the new bone formation guide layer is 40:60 to 10:90 as the mass ratio.

11. The production method according to claim 10, further comprising a step of roughening treatment of the surface of the non-bioabsorbable organic base material.

12. The production method according to claim 10, wherein the mixture comprising a hydrophilic polymer and calcium phosphate is coated on the non-bioabsorbable organic base material with a thickness of 10 to 200 μm.

13. The production method according to claim 10, wherein the mixture comprising a hydrophilic polymer and calcium phosphate is coated on the non-bioabsorbable organic base material with a thickness of 20 to 80 μm.

14. The production method according to claim 10, wherein the mixture comprising a hydrophilic polymer and calcium phosphate is coated on the non-bioabsorbable organic base material with a thickness of 30 to 60 μm.

15. The production method according to claim 10, wherein the proportion of the contents of the hydrophilic polymer and the calcium phosphate in the mixture is 40:60 to 10:90 as the mass ratio.

16. The production method according to claim 10, wherein the proportion of the contents of the hydrophilic polymer and the calcium phosphate in the mixture is 30:70 to 15:85 as the mass ratio.

* * * * *